(12) United States Patent
Susilo et al.

(10) Patent No.: US 6,943,185 B2
(45) Date of Patent: Sep. 13, 2005

(54) USE OF 2-METHYL-THIAZOLIDINE-2, 4-DICARBOXYLIC ACID AND/OR PHYSIOLOGICALLY COMPATIBLE SALTS THEREOF FOR PRODUCING A MEDICAMENT FOR TREATING CANCERS

(75) Inventors: Rudy Susilo, Köln (DE); Hans Rommelspacher, Berlin (DE)

(73) Assignee: Trommsdorff GmbH & Co. KG, Alsdorf (DE)

( * ) Notice: Subject to any disclaimer, the term of this patent is extended or adjusted under 35 U.S.C. 154(b) by 334 days.

(21) Appl. No.: 10/182,442

(22) PCT Filed: Feb. 15, 2001

(86) PCT No.: PCT/DE01/00656

§ 371 (c)(1), (2), (4) Date: Dec. 10, 2002

(87) PCT Pub. No.: WO01/60343

PCT Pub. Date: Aug. 23, 2001

(65) Prior Publication Data

US 2003/0149085 A1 Aug. 7, 2003

(30) Foreign Application Priority Data

Feb. 15, 2000 (EP) .......................... 100 08 159

(51) Int. Cl.$^7$ ................................................ A61K 31/41
(52) U.S. Cl. ........................................................ 514/365
(58) Field of Search ......................................... 514/365

(56) References Cited

U.S. PATENT DOCUMENTS 6,303,642 B1 * 10/2001 Susilo et al. ................ 514/365
6,441,011 B1 *  8/2002 Susilo et al. ................ 514/369

FOREIGN PATENT DOCUMENTS

WO          98 38994 A       8/1998

OTHER PUBLICATIONS

Carter et al., Chemotherapy of Cancer, Second Edition, John Wiley & Sons, N.Y., N.Y., 1981, pp 342 and 362–365.*
L.B. Wlodek et al., NEOPLASMA, vol. 43, No. 4, pp. 259–263, (1996).

* cited by examiner

Primary Examiner—Rebecca Cook
(74) Attorney, Agent, or Firm—Birch, Stewart, Kolasch & Birch, LLP

(57) ABSTRACT

Use of 2-methyl-thiazolidine-2,4-dicarboxylic acid (2-MTDC) and/or its physiologically tolerable salts for the treatment and/or prevention of cancer.

6 Claims, No Drawings

USE OF 2-METHYL-THIAZOLIDINE-2, 4-DICARBOXYLIC ACID AND/OR PHYSIOLOGICALLY COMPATIBLE SALTS THEREOF FOR PRODUCING A MEDICAMENT FOR TREATING CANCERS

This application is the national phase under 35 U.S.C. § 371 of PCT International Application No. PCT/DE01/00656 which had an International filing date of Feb. 15, 2001, which designated the United States of America.

This invention relates to the use of 2-methyl-thiazolidine-2,4-dicarboxylic acid (2-MTDC) and/or its physiologically tolerable salts for the treatment and/or prevention of cancer.

The method is useful in the treatment of cancers of the internal organs, pulmonary, gastric, pancreatic, renal and hepatic carcinomas and mammary, skin, bladder, esophageal and tracheal cancer.

According to statistics, cancer has moved from the seventh to the second place among the causes of death in industrial nations. Despite an enormous research effort, about 160,000 people die from cancer in Germany each year. About 600,000 new cancer patients are diagnosed each year in the United States.

The chances of fighting cancer are determined by personal risk factors and by the options of therapeutic intervention available.

Many known cancer-fighting agents have strong side effects which weaken and/or damage healthy organs during cancer treatment.

Thus there is an urgent need to provide substances for cancer treatment and prevention that do not have strong side effects.

It is therefore the problem of this invention to provide a physiologically tolerable substance for cancer treatment and prevention.

This problem is solved according to the invention by using 2-methyl-thiazolidine-2,4-dicarboxylic acid (2-MTDC) and/or its physiologically tolerable salts as a tolerable substance for the treatment and/or prevention of cancer.

The synthesis of 2-methyl-thiazolidine-2,4-dicarboxylic acid (2-MTCD), its use as a hepaprotective agent, and the manufacture of pharmaceuticals in the form of lozenges or ointments containing 2-methyl-thiazolidine-2,4-dicarboxylic acid (2-MTCD) are known from DE-OS 21 16 629. 2-MTCD has been proposed as a pharmaceutical for several uses. EP 989 16 811 discloses a use of 2-methyl-thiazolidine-2,4-dicarboxylic acid(2-MTDC) as a mucolytic, and EP 989 16 809 describes a combination of 2-methyl-thiazolidine-2,4-dicarboxylic acid (2-MTDC) and paracetamol.

Nothing was known as yet about the favorable influence of 2-methyl-thiazolidine-2,4-dicarboxylic acid (2-MTDC) and its physiologically tolerable salts on cancer prevention and treatment and/or on reducing the side effects of cytostatics.

Surprisingly, it was found that 2-methyl-thiazolidine-2, 4-dicarboxylic acid (2-MTDC) and/or its physiologically tolerable salts can be effectively used for the treatment and/or prevention of cancer.

Animal tests proved that 2-methyl-thiazolidine-2,4-dicarboxylic acid (2-MTDC) and/or its physiologically tolerable salts can slow down or even stop the advance of cancerous diseases.

These studies were conducted in several animal tumor models. Test systems used were the mouse, the rat, and the hamster. The objects of study included skin papillomas, mammary adenocarcinomas, tracheal cancer, pulmonary adenocarcinomas as well as colon carcinomas and bladder cancer.

The way in which 2-methyl-thiazolidine-2,4-dicarboxylic acid (2-MTDC) acts has not yet been completely understood. It is assumed, however, that 2-methyl-thiazolidine-2,4-dicarboxylic acid (2-MTDC) serves as a prodrug for the release of L-cysteine which subsequently is converted into glutathione (γ-glutamylcysteinyl-glycine, GSH), an agent that commonly is ascribed the function of a radical trap.

Thus a preventive approach to cancer is that mutagenic substances such as nitrite or nitroso compounds are caught by the radical trap before they can unfold their damaging effect in the body. This is achieved by means of endogenic glutathione (GSH) or synthetic N-acetylcysteine (NAC).

Colon bacteria are a relevant source of endogenic glutathione (GSH). Doctors should make it a point during cancer treatment to protect the endogenic sources of glutathione or other radical traps and not weaken them by, for example, a chemotherapy, in order to prevent any additional reduction in glutathione (GSH) supply.

Glutathione (γ-glutamylcysteinylglycine, GSH) is the most important natural substance that can capture and eliminate cytotoxic oxygen radicals that are formed in numerous oxidative enzyme reactions. Each cell of the human body contains high concentrations of glutathione (GSH), which is understandable as otherwise the oxygen radicals that were formed would destroy components of the cell membrane and block other intracellular processes such as gene repair mechanisms. Uninhibited action of oxygen radicals results in cell destruction.

As reactive oxygen species (oxygen radicals) accelerate carcinogenesis, trapping these molecules is another mechanism by which glutathione (GSH) has a preventive effect.

A similar effect has been ascribed to N-acetylcysteine. N-acetylcysteine contains a masked form of L-cysteine that can be converted into glutathione (GSH) after it has been released in the body.

Furthermore, another important protective effect of glutathione (GSH) and N-acetylcysteine (NAC) has been observed in conjunction with cancerogenesis. Researchers found that the destruction of genetic material by radiation and carcenogenics (e.g. 2AAF) can be reduced if N-acetylcysteine (NAC) is administered simultaneously.

In addition to these protective effects, glutathione (GSH) can also reduce the growth of existing tumors. N-acetylcysteine (NAC) also proved effective in animal tumor models. Patients with pulmonary or mammary cancer showed reduced levels of L-cysteine and other amino acids in the blood at a relatively early stage of the disease (Zhang P. C., Pang C. P., Clin. Chem. 38, pp. 1198–1199, 1992). Such a reduction was also found in C57BL/6 mice with a fibrosarcoma (Hack V., Gross A., Kinscherf R., Bockstette M., Fiers W., Becke G. and Dröge W., FASEB J. 10, pp. 1219–1226, 1996).

The mechanisms of this effect are still not very well understood. Researchers observed that N-acetylcysteine (NAC) inhibits spontaneous mutations as may be induced by irradiation and the formation of complexes of carcinogenic substances and genetic material (DNA). These studies also found that N-acetylcysteine (NAC) delays the development of tumors or suppresses them completely.

Another promising application is the reduction of undesirable effects of cytostatics by administering thiol-containing substances. For example, pulmonary cancer patients were treated with epirubicin. When they were simultaneously treated with N-acetylcysteine (NAC), the undesirable cardiotoxic effects of epirubicin could be prevented (Cipri A., Peverini M., Schiavo B. and Pozzar F., Eur. Respiration J. 7 (Suppl. 8) 391s 1994).

A long-term study conducted in Europe and involving multiple centers tested N-acetylcysteine (NAC) as a preventive pharmaceutical in high-risk pulmonary carcinoma patients (EUROSCAN). The results showed that N-acetylcysteine (NAC) proved promising for this indication at least on research level (Van Zandwijk N., J. of Cellular Biochemistry 58, Suppl. 22, pp. 24–32, 1995).

The way in which 2-methyl-thiazolidine-2,4-dicarboxylic acid (2-MTDC) acts is not fully understood as yet. However, we can assume that N-acetylcysteine has an equivalent mechanism that leads to the key molecule, glutathione (GSH). Glutathione is capable of putting radicals, primarily oxygen radicals, out of action.

Based on assuming this somewhat incomplete mechanism of action that still leaves many questions unanswered, studies should primarily focus on the provision and use of substances that, in a controlled way and without the occurrence of toxic products, release L-cysteine in the quantity required and at the right place.

The known compounds that are used as yet and that represent the state of the art do this job inadequately at best.

For the treatment approach, it would be the obvious solution to apply the natural substance, glutathione (GSH). But the use of glutathione itself is out of the question as it would be destroyed in the stomach and could not be transported into the cells. The cells do not have an appropriate transport mechanism for this.

Direct application of L-cysteine also has to be ruled out because L-cysteine is toxic as has been shown in cell cultures as well as in newborn mice and rats. Applying toxic L-cysteine results in necrobiosis of brain cells (Karlsen R. L., Grofova Y., Malthe-Sorensen D. and Farnum E., Exp. Brain. Res. 208, pp. 167–180, 1981). This toxicity can be bypassed if a so-called prodrug is applied, i.e. a predecessor pharmaceutical from which the effective amino acid is released in a controlled way inside the body.

So glutathione (GSH) or L-cysteine have to be replaced by progenitors that can be converted into L-cysteine in the body which then becomes available for glutathione synthesis. The best known progenitor is N-acetylcysteine (NAC).

Only a minor portion of L-cysteine is released from N-acetylcysteine by hydrolysis. The major portion is released by an amino acid N-deacylase which was detected, for example, in the cytosol of hepatic cells (Wlodek, L., Rommelspacher, H., Susilo, R., Radomski, J. and Hefle, G., Biochem. Pharmacol. 46 pp. 917–928 (1993)).

It is generally assumed that N-acetylcysteine (NAC) is a low-toxic pharmaceutical. However, some barely known reports prove that the toxicity risk N-acetylcysteine poses is underestimated (Estrela, J. M., Saez, G. T., Such, L. and Vina, J., Biochem. Pharmacol. 32, pp. 3483–3485 (1983), and Vina, J., Romero, F. J., Saez, G. T. and Pallardo, F. V., Experientia 39, pp. 164–165 (1983)).

This risk of a toxic reaction makes it inevitable to look for alternatives to N-acetylcysteine (NAC).

Thiazolidines that are a precursor drug of glutathione (GSH) could be such an alternative to N-acetylcysteine (NAC).

The condensation of carbonyl-containing substances with L-cysteine into thiazolidines has been described before (Susilo, R., Rommelspacher, F. and Hoefle, G., J. Neurochem. 52, pp. 1793–1800 (1989)). It is important in this context that said thiazolidines form an L-cysteine reservoir from which the amino acid can be released as required.

An example of a simply structured thiazolidine is the condensation product of formaldehyde and L-cysteine. Metabolites of this substance proved to be neurotoxic, however.

The condensation product of acetaldehyde and L-cysteine is not suited as a predecessor pharmaceutical because it spontaneously decomposes into its components under physiological conditions (Wlodek, L., Rommelspacher, H., Susilo, R., Radomski, J. and Hefle, G., Biochem. Pharmacol. 46, pp. 917–928 (1993)).

As the thiazolidines described do not meet the pharmacological requirements, we must search for thiazolidine derivatives that can be used as pharmaceuticals.

Researchers have now found out that the condensation product of pyruvic acid and L-cysteine meets the requirements best.

When L-cysteine is released from 2-methyl-thiazolidine-2,4-dicarboxylic acid (2-MTDC), the byproduct is a physiologically harmless pyruvate. Pyruvate is a physiological substance that is completely harmless at the quantities it is released in the body. Unlike N-acetylcysteine (NAC), 2-methyl-thiazolidine-2,4-dicarboxylic acid is therefore very well tolerated. There are even indications that pyruvate has a protective effect (Rastellini, C., Cicalese, L., Zeevi, A., Mattes, C., Stauko, R. T., Starzl, T. E. and Rao, A. S., Transplant. Proceed. 27, pp. 3383–3384 (1995)). Pyruvate is formed from glucose in physiological conditions and is needed in the tricarboxylic acid cycle for producing the cell's energy.

It was surprisingly found that the treatment with 2-methyl-thiazolidine-2,4-dicarboxylic acid (2-MTDC) does not only prevent the cellular immune system from destruction, as was shown for liver cells (Wlodek L. and Rommelspacher H., Alcohol and Alcoholism 29, pp. 649–657, 1994), but that this protective effect of 2-methyl-thiazolidine-2,4-dicarboxylic acid (2-MTDC) is fairly long-lasting.

Release of L-cysteine and formation of glutathione (GSH) could be detected in hepatic tissue of mice after 12 hours (2-MTDC 1.2 mmol/kg, intraperitoneally administered) and raised the GSH level to 112.0% (P<0.01) after 12 hours. Intraperitoneal application of 2.4 mmol 2-MTDC per kg of whole-body wet weight resulted in a GSH level increase in the liver to 154.5% of the reference values, P<0.001. The test results are presented in Table 1.

TABLE 1

Effect of 2-methyl-thiazolidine-2,4-dicarboxylic acid (2-MTDC) on reduced glutathione (GSH) in the hepatic tissue in mice

| Time after injection (hours) | Reference value 0.9% NaCl ($\bar{x}$ ± SD) | Glutathione (GSH)-μmol/g wet weight | | | |
|---|---|---|---|---|---|
| | | 2-MTDC (1.2 mmol/kg) | | 2-MTDC (2.4 mmol/kg) | |
| | | ($\bar{x}$ ± SD) | % of the reference value | ($\bar{x}$ ± SD) | % of the reference value |
| 1 | 6.45 ± 0.42 | 7.62[b] ± 0.37 | 117.5 | 8.27[a] ± 0.33 | 127.6 |
| 4 | 6.38 ± 0.25 | 5.56[c] ± 0.42 | 87.2 | 5.76 ± 0.42 | 90.3 |

TABLE 1-continued

Effect of 2-methyl-thiazolidine-2,4-dicarboxylic acid (2-MTDC) on reduced glutathione (GSH) in the hepatic tissue in mice

| Time after injection (hours) | Reference value 0.9% NaCl ($\bar{x}$ ± SD) | Glutathione (GSH)-μmol/g wet weight | | | |
|---|---|---|---|---|---|
| | | 2-MTDC (1.2 mmol/kg) | | 2-MTDC (2.4 mmol/kg) | |
| | | ($\bar{x}$ ± SD) | % of the reference value | ($\bar{x}$ ± SD) | % of the reference value |
| 8 | 5.97 ± 0.29 | 6.48 ± 0.67 | 108.5 | 6.69$^c$ ± 0.32 | 112.0 |
| 12 | 4.73 ± 0.31 | 5.77$^b$ ± 0.30 | 112.0 | 7.31$^c$ ± 0.41 | 154.5 |

$^a$P < 0.001
$^b$P < 0.01
$^c$P < 0.02
$^d$P < 0.05
The mean values [$\bar{x}$] (± standard deviation [SD]) were compared using a Student's t-test to establish a statistical difference;
n = 2; five to six mice per group.

These observations point to the release of L-cysteine from 2-methyl-thiazolidine-2,4-dicarboxylic acid (2-MTDC) controlled by enzymes. The result is that the quantity of L-cysteine released is adjusted to the respective body and is dosage-dependent. This prevents the very high concentrations of toxic L-cysteine that can be observed after a long-term treatment with N-acetylcysteine (NAC). It also contributes to making 2-methyl-thiazolidine-2,4-dicarboxylic acid (2-MTDC) more tolerable.

The enzymatically controlled release of L-cysteine from 2-methyl-thiazolidine-2,4-dicarboxylic acid (2-MTDC) and the splitting-off of physiologically harmless pyruvate for a controlled dosage-dependent supply of L-cysteine needed by the system makes 2-methyl-thiazolidine-2,4-dicarboylic acid (2-MTDC) clearly superior to any known compounds such as N-acetylcysteine (NAC).

The toxic side-effects known from N-acetylcysteine (NAC) can be considerably reduced by using 2-methyl-thiazolidine-2,4-dicarboxylic acid (2-MTDC).

If we base this on what has been found out so far about the way in which N-acetylcysteine (NAC) acts, we can understand that 2-methyl-thiazolidine-2,4-dicarboxylic acid (2-MTDC) causes a reduction in free radicals and an increase in the concentration of sulfhydryl groups in the system. This results in a cytoprotective effect of this compound.

2-Methyl-thiazolidine-2,4-dicarboxylic acid (2-MTDC) therefore reduces the side effects of cytostatics by diminishing or eliminating the thiol group deficit that manifests itself by a L-cysteine and/or glutathione (GSH) shortage.

The application of 2-methyl-thiazolidine-2,4-dicarboxylic acid (2-MTDC) for preventing cancer or halting the advance of cancer and for reducing undesirable side effects of a cytostatics treatment is therefore useful from a medical and a scientific point of view and highly recommended.

We claim:

1. A method of treating cancer in a patient in need thereof, which comprises administering an effective amount of 2-methyl-thiazolidine-2,4-dicarboxylic acid (2-MTDC) and/or one or more of its physiologically tolerable salts to said patient.

2. The method of claim 1, wherein the method is for treating cancer of internal organs in a patient.

3. The method of claim 1, wherein the method is for treating cancer is selected from the group consisting of pulmonary, gastric, pancreatic, renal and hepatic carcinomas.

4. The method of claim 1, wherein the method is for treating cancer is selected from the group consisting of mammary, skin, bladder, esophageal and tracheal cancer.

5. A method of treating cancer in a patient in need thereof, which comprises administering an effective amount of 2-methyl-thiazolidine-2,4-dicarboxylic acid (2-MTDC) and/or one or more of its physiologically tolerable salts to said patient, wherein the cancer is selected from the group consisting of pulmonary, gastric, pancreatic, renal and hepatic carcinomas, and mammary, skin, bladder, esophageal and tracheal cancer.

6. The method of claim 5, wherein the cancer is responsive to treatment with 2-MTDC.

* * * * *